United States Patent
Kelly et al.

(10) Patent No.: US 6,383,163 B1
(45) Date of Patent: *May 7, 2002

(54) ELECTRIC BREAST PUMP DESIGNED TO SIMULATE INFANT SUCKLING

(76) Inventors: Patricia Ann Kelly, 2545 Keystone St.; Joan Patricia Ortiz, 1930 N. Valley St., both of Burbank, CA (US) 91504

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/304,364

(22) Filed: May 4, 1999

Related U.S. Application Data

(60) Provisional application No. 60/084,054, filed on May 4, 1998.

(51) Int. Cl.[7] .................................................. A61M 1/06
(52) U.S. Cl. .............................. 604/74; 604/73; 604/118
(58) Field of Search ..................... 604/73, 74, 118–120, 604/131, 540; 417/306, 307, 440

(56) References Cited

U.S. PATENT DOCUMENTS

| | | | |
|---|---|---|---|
| 4,772,262 A | | 9/1988 | Grant et al. |
| 4,961,726 A | * | 10/1990 | Richter .......................... 604/74 |
| 5,071,403 A | | 12/1991 | Larsson |
| 5,380,280 A | * | 1/1995 | Peterson ....................... 604/65 |
| 5,419,768 A | * | 5/1995 | Kayser ......................... 604/119 |
| 5,571,084 A | | 11/1996 | Palmer |
| 5,624,394 A | * | 4/1997 | Barnitz et al. ................. 604/67 |
| 5,676,525 A | | 10/1997 | Berner et al. |
| 5,795,328 A | * | 8/1998 | Bartnitz et al. ............... 604/67 |
| 5,810,772 A | * | 9/1998 | Niederberger ............... 604/74 |
| 5,902,267 A | * | 5/1999 | Medo .......................... 604/74 |
| 5,954,690 A | * | 9/1999 | Larsson ....................... 604/74 |
| 6,045,529 A | * | 4/2000 | Nüesch ........................ 604/74 |

FOREIGN PATENT DOCUMENTS

DE      38 20 211 A      6/1988

OTHER PUBLICATIONS

Comparing breastfeeding and Breast Pumps using a Computer Model, Chrishopher Zoppou, Ph.d. et al., J Hum Lact 13(3), Mar. 25, 1997.

* cited by examiner

Primary Examiner—Corrine McDermott
Assistant Examiner—Cris L. Rodriguez
(74) Attorney, Agent, or Firm—Price and Gess

(57) ABSTRACT

An electric breast pump utilizes an electric motor to drive a piston vacuum pump to draw a negative pressure or suction up to 250 mm Hg at a flexible collapsible breast cup. The suction cycles between the set maximum and atmospheric under the control of a magnetic valve that is opened and closed by a vacuum sensor. The valve opens and closes a bypass to atmosphere. The speed of the electric motor can be selectively varied to increase the frequency of the suction cycles, which can vary between 20 to 44 cycles per minute. The breast cup collapses during a part of each cycle to simulate the peristaltic action of a suckling infant.

20 Claims, 2 Drawing Sheets

ELECTRIC BREAST PUMP DESIGNED TO SIMULATE INFANT SUCKLING

CROSS-REFERENCE TO RELATED APPLICATIONS

This application is a continuation of U.S. provisional application Ser. No. 60/084,054 for PJ's Comfort Electric Breast Pump and Soft Breast Cup, filed on May 4, 1998, now abandoned.

BACKGROUND OF THE INVENTION

1. Field of the Invention

The present invention relates generally to improvements in breast pumps, and more particularly pertains to new and improved electric breast pumps wherein the breast pump both expresses and collects breast milk.

2. Description of Related Art

In the field of breast pumps for expressing breast milk it has been the practice to employ hard breast cups and maximum suction to the human teat to express the breast milk. Such devices have not been entirely satisfactory in that if the suction generated by the breast pump is too high, bruising will be caused to the areola and nipple. In addition, the amount of milk volume obtained in response to a constant average suction is quite low compared to that obtained by a suckling infant. A breast feeding infant, in addition to applying suction, compresses the teat against his hard palate and uses the peristaltic action of the tongue. A research study entitled *Comparing Breastfeeding and Breast Pumps Using a Computer Model*, published in the Journal of Human Lactation, 1997, Vol. 13, pp. 195 to 202, by Christopher Xoppou, Ph.D., et al., concluded that a large increase in milk flow can be obtained when both cyclic suction and peristaltic force is used on the human teat. The present invention simulates an infant suckling by utilizing both peristaltic forces and cyclic suction.

SUMMARY OF THE INVENTION

The objects of the present invention are achieved by use of soft breast cups made of durable, yet flexible, plastic material that collapse around the human teat during a portion of each suction cycle. Suction is created by an electric motor driving a piston vacuum pump that draws a continuous suction airflow. The suction cycle is caused by a magnetic valve controlled by a vacuum sensor that causes the valve to open the vacuum line to atmosphere when a pre-set maximum pressure is reached and closes again when pressure is released. Motor speed and maximum pressure is selectable by the user. The suction may be adjusted between 150 mm Hg to 250 mm Hg. The motor speed is adjustable between these different speeds to vary the suction frequency from about 20 to 44 cycles per minute. The suction and cycle adjustment, along with the flexible, collapsing cups, provides for greater comfort and optimized milk flow. Besides collection bottles, one for each of the two breast cups, the system uses a catch bottle in the suction tube, before it is connected to the vacuum pump, to catch any breast milk that happens to accidentally flow past a collection bottle. The catch bottle prevents the breast milk from entering the vacuum pump. Milk flow into the catch bottle will trigger a light sensor that causes the motor to stop.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts throughout the figures thereof, and wherein.

DETAILED DESCRIPTION OF THE PREFERRED EMBODIMENTS

The following description is provided to enable any person skilled in the art to make and use the invention and sets forth the best modes contemplated by the inventor for carrying out the invention. Various modifications, however, will remain readily apparent to those skilled in the art, since the basic principles of the present invention have been defined herein specifically to provide an electronic inductor circuit suitable for high-speed modem applications.

Figure 1:
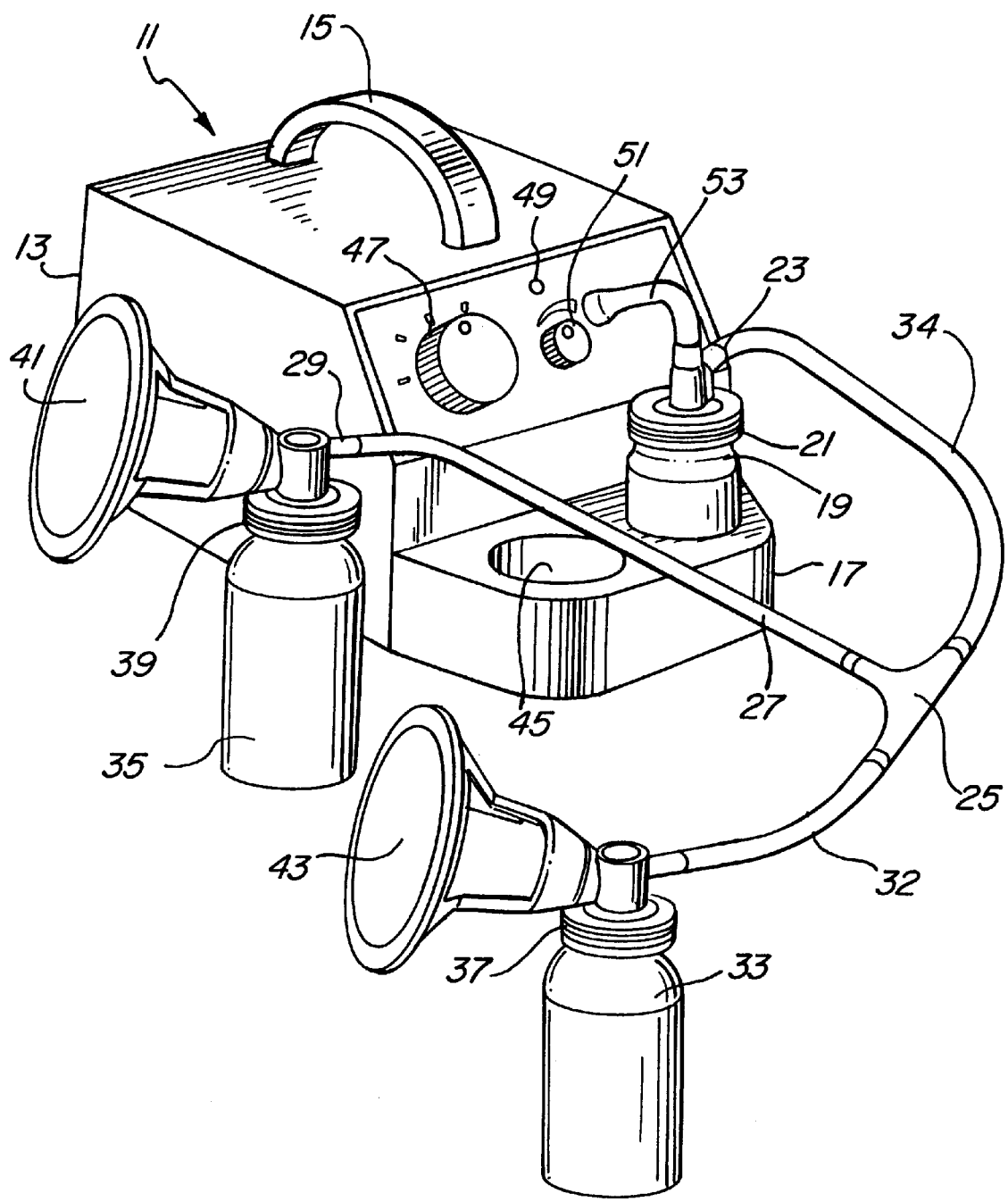
FIG. 1 is a perspective illustration of the basic elements of a preferred embodiment of the present invention.

Referring now to FIG. 1, the breast pump 11 of the present invention is illustrated as contained within a housing 13, preferably made of a lightweight plastic, having a handle 15 to facilitate easy movement of the breast pump 11. The housing 13 has a tray 17 mounted to its front which contains a pair of bottle holder apertures 45 for holding a catch bottle 19 and additional collection bottles, as desired.

Two breast cups 41, 43 may be advantageously used with the breast pump of the present invention. Each breast cup 41, 43 is made of a soft flexible, but sturdy, plastic material which is shaped to comfortably fit over the human teat and a portion of the breast. Each breast cup is associated with a collection bottle. Breast cup 41 is connected to a vacuum tube 27 by a tube connector 29 that also connects to the interior of collection bottle 35 by a removable bottle cap 39. Flexible breast cup 43 likewise is connected to collection bottle 33 by removable bottle cap 37, both of which are connected to a tube connector 31. Tube connector 31 is connected to vacuum line 32. Vacuum line 27 from breast cup 41 and line 32 from breast cup 43 are both connected to a Y-connection 25 which connects both lines 27, 32 to a vacuum line 34 leading to tube connector 23 which is connected to removable bottle top 21. Connector 23 is also connected to vacuum tube 53 which leads to a vacuum pump, which will be discussed hereinafter. Removable bottle top 21 is sealably attached to catch bottle 19. A light sensor is located on the underside of bottle top 21, positioned to detect the passage of fluid into the catch bottle.

Housing 13 of breast pump 11 carries a pair of adjustment knobs 47 and 51 and an "on" light 49. Adjustment knob 47 controls the speed of the electric motor inside housing 13 which drives the vacuum pump, also inside housing 13, thereby varying the suction cycles administered to the human teat by the vacuum being drawn through the breast cups 41, 43. The other adjustment knob 51 is a vacuum or suction adjustment which allows the user to set the maximum continuous suction or vacuum being applied to the human teat within the breast cups 41, 43. By providing both a user-settable cycle adjustment and vacuum adjustment, the breast pump of the present invention can be adjusted by the user to provide for the greatest amount of comfort and maximum milk flow.

Vacuum adjustment knob 51 allows the user to select from a range of maximum suction levels from about between 150 mm Hg to 250 mm Hg, which is continuously generated at the breast cups 41, 43. The cycle adjustment knob 47 allows the user to adjust the speed of the motor driving the vacuum pump. This tends to vary the number of suction cycles per minute administered to a human teat by the suction cup 41, 43. The preferred frequency range of cycles is between 20 to 44 cycles per minute. During each cycle, the breast cup 41 collapses around the human teat when suction reaches its maximum, as set by the user by knob 51, and recovers again during the period of the cycle that the vacuum line 53 is vented to the atmosphere.

Figure 2:
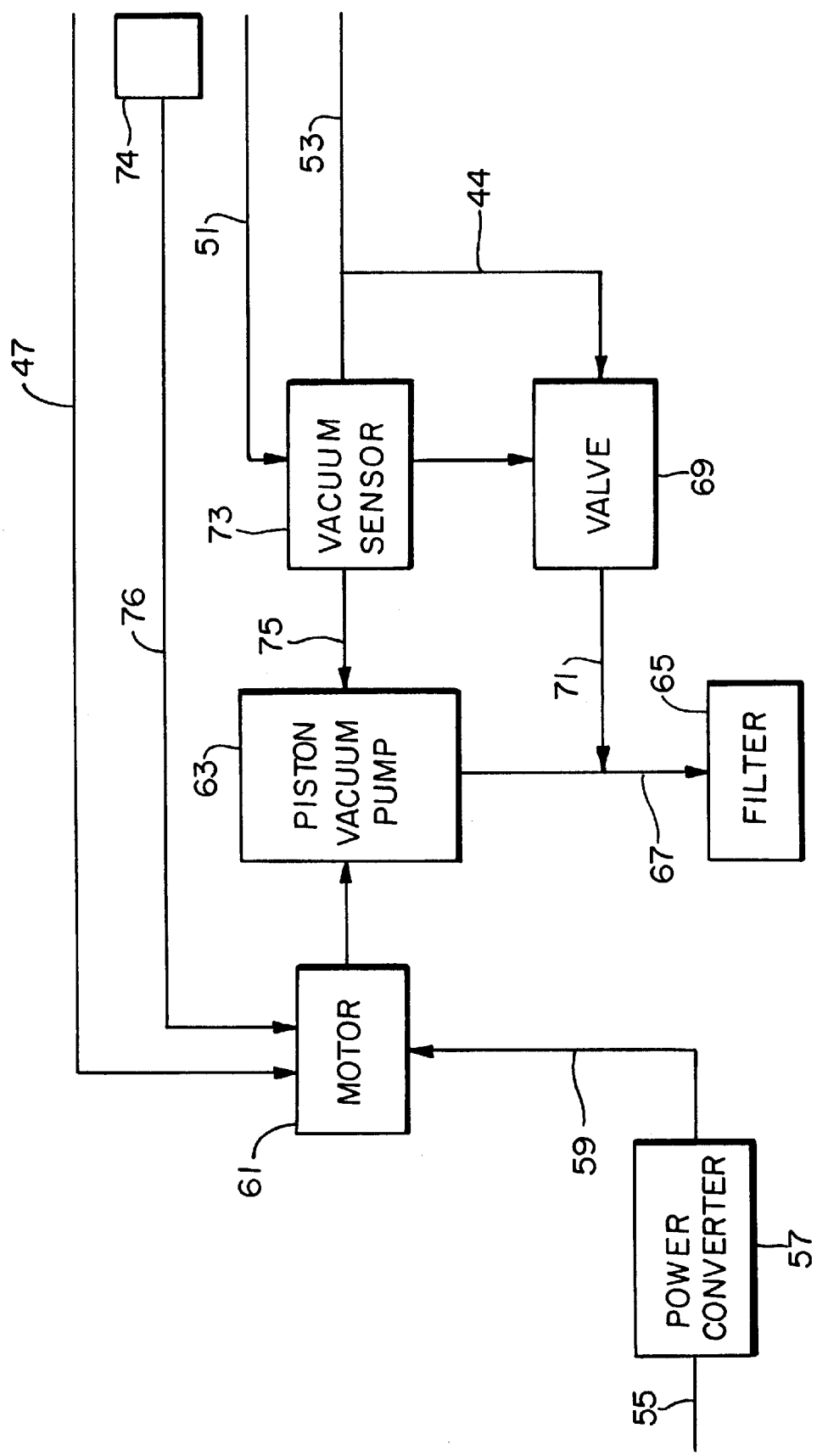
FIG. 2 is a block diagram showing the operative elements of the present invention.

The elements of breast pump 11 contained within housing 13 are a 12-volt electric motor 61 (FIG. 2) that is powered by a power converter 57, that may be connected to a 115-volt 60 Hz outlet and provides a 12-volt DC source over line 59 to motor 61. Motor 61 drives a piston vacuum pump 63 which has a vacuum intake line 75 and an exhaust line 67. Exhaust line 67 is vented to the atmosphere through a filter 65 which is preferably a hydrophobic PTFE membrane filter or any other filter capable of controlling particle size of 0.02 microns. Vacuum intake line 75 for a piston vacuum pump 63 is connected to a vacuum sensor 73 which senses the maximum suction in vacuum line 53, which is connected to the breast cups 41, 43 (FIG. 1). Vacuum sensor 73 is preferably an electronic difference pressure sensor, or any other device which can readily detect the maximum pressure or suction in the vacuum line 53. An electromagnetic valve 69 is connected to vacuum line 53, in a bypass loop to piston pump 63. The bypass loop is made up of vacuum line 44 at its intake, and vacuum line 71 at its outlet, which is connected to outlet line 67 leading to the atmosphere through filter 65.

Vacuum sensor 73 is adjustable by adjustment knob 51. Electric motor 61 is likewise adjustable by adjustment knob 47. In addition, motor 61 is turned off over control line 76 whenever light sensor 74 in the catch bottle detects that fluid is flowing into catch bottle 19.

The breast pump of the present invention provides both a cyclic suction and peristaltic forces, the combination closely resembles the suckling of an infant. The result is an increase in milk volume over prior art breast pumps, while allowing the user to adjust the breast pump for the greatest degree of comfort.

The cycling of the continuous suction air flow is the result of the magnetic valve 69 which is controlled by the electronic vacuum sensor 73. The magnetic valve 69 opens or closes a bypass line 44, 71 to atmosphere through exhaust line 67 and filter 65. Each time the magnetic valve 69 opens, vacuum line 53 exhausts to the atmosphere, causing the breast cups 41, 43 to recover from the collapsed state. When vacuum sensor tells electromagnetic valve 69 to close, the motor and piston vacuum pump drive the suction in vacuum line 53 back up to its set maximum, causing breast cups 41, 43 to collapse. Once maximum suction is reached, vacuum sensor 73 again tells valve 69 to open, exhausting the suction in vacuum line 53 to atmosphere once again. The cycle frequency may be varied from about 22 cycles per minute to 44 cycles per minute, depending on whether one or two collection bottles are in the vacuum circuit, the speed setting for motor 61, and the maximum vacuum setting for vacuum sensor 73. The faster the motor 61 is driving piston pump 63, the faster maximum suction is obtained in vacuum line 53 and cups 41, 43. The maximum suction setting which can be adjusted continuously between 150 mm of Hg to 250 mm of Hg will also impact the cycle frequency. As the collection bottles 35, 33 fill up with breast milk, thereby reducing the volume that needs to be evacuated by the piston vacuum pump 63, the cycle frequently will increase.

What has been described is an electric breast pump that most nearly simulates the suckling of an infant on a human teat by applying both cyclic suction and peristaltic force to the human teat by flexible and collapsible breast cups. Moreover, the maximum suction is readily selectable by the user for optimum comfort. Regardless of the suction level selected, the system prevents the accidental flow of breast milk into the pump.

Those skilled in the art will appreciate that various adaptations and modifications of the just-described preferred embodiment can be configured without departing from the scope and spirit of the invention. Therefore, it is to be understood that within the scope of the appended claims, the invention may be practiced other than as specifically described herein.

What is claimed is:

1. A breast pump for extracting breast milk from a human teat, comprising:
   a motor;
   a vacuum pump driven by said motor;
   a flexible plastic breast cup connected to the vacuum pump by a tube;
   a bypass valve for venting the suction created in the breast cup to atmosphere; and
   a vacuum sensor for sensing the suction in the breast cup and opening the bypass valve when maximum suction is sensed, and closing the bypass valve when the suction is released.

2. The breast pump of claim 1 wherein said motor comprises a manual speed adjustment, selectable by the user.

3. The breast pump of claim 1 wherein said vacuum sensor comprises a manually settable maximum suction.

4. The breast pump of claim 1 wherein the manually settable maximum suction is adjustable over a range.

5. The breast pump of claim 1 wherein said breast cup collapses during maximum suction and recovers when suction is released.

6. The breast pump of claim 1 further comprising a collection bottle connected to the breast cup and the tube to the vacuum pump so that the vacuum pump draws a suction in the collection bottle and the breast milk flows directly into the bottle.

7. The breast pump of claim 6 further comprising a catch bottle connected between the collection bottle and the vacuum pump so that the vacuum pump draws a suction in the catch bottle.

8. The breast pump of claim 7 further comprising a filter in the vent line between the vacuum pump and atmosphere, and between the bypass valve and atmosphere.

9. The breast pump of claim 8 wherein the filter material is a hydrophobic PTFE membrane.

10. The breast pump of claim 9 wherein said motor is an electric motor.

11. The breast pump of claim 10 wherein the electric motor is a 12-volt motor.

12. The breast pump of claim 11 further comprising a power converter circuit for converting a 115-volt, 60 Hz supply, to 12 volts DC.

13. A breast pump for extracting milk from a human teat, comprising:
   a flexible plastic breast cup for placement over a human teat;
   a vacuum pump having an intake for driving a continuous air suction;
   an electric motor connected to a source of power and to the vacuum pump for driving the vacuum pump;
   a tube connecting the intake of the vacuum pump and breast cup to allow the vacuum pump to draw a suction on the breast cup;

a vacuum sensor connected to the tube between the breast cup and the vacuum pump for sensing whether suction has reached a maximum; and a bypass valve connected to the tube between the breast cup and the vacuum pump for venting the suction in the tube to atmosphere when the sensor senses maximum suction.

14. The breast pump of claim 13 wherein said breast cup collapses during maximum suction and recovers when the suction is released.

15. The breast pump of claim 13 wherein said electric motor comprises a manual speed adjustment, selectable by the user.

16. The breast pump of claim 13 wherein said vacuum sensor comprises a manually settable maximum suction.

17. The breast pump of claim 13 further comprising a collection bottle connected to the breast cup and the tube so that the vacuum pump draws a suction in the collection bottle.

18. The breast pump of claim 17 further comprising:

a second flexible plastic breast cup for placement over a human teat;

a second plastic tube connecting the second flexible plastic breast cup to the plastic tube connected to the intake of the vacuum pump, to allow the vacuum pump to draw a suction on both breast cups.

19. The breast pump of claim 18 further comprising a second collection bottle connected to the second breast cup and the tube so that the vacuum pump draws a suction in the second collection bottle.

20. The breast pump of claim 17 farther comprising a catch bottle connected to the tube between the collection bottle and the vacuum pump so that the vacuum pump draws a suction in the catch bottle.

* * * * *